(12) United States Patent
Tran et al.

(10) Patent No.: US 9,731,141 B2
(45) Date of Patent: *Aug. 15, 2017

(54) MULTI-ELEMENT ACOUSTIC RECHARGING SYSTEM

(71) Applicant: Cardiac Pacemakers, Inc., St. Paul, MN (US)

(72) Inventors: Binh C. Tran, Minneapolis, MN (US); Bin Mi, Plymouth, MN (US); Robert S. Harguth, Ham Lake, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 284 days.

This patent is subject to a terminal disclaimer.

(21) Appl. No.: 13/725,405

(22) Filed: Dec. 21, 2012

(65) Prior Publication Data

US 2013/0110192 A1 May 2, 2013

Related U.S. Application Data

(63) Continuation of application No. 12/611,686, filed on Nov. 3, 2009, now Pat. No. 8,340,778, which is a continuation of application No. 12/128,396, filed on May 28, 2008, now Pat. No. 7,634,318.

(60) Provisional application No. 60/943,939, filed on Jun. 14, 2007.

(51) Int. Cl.
*A61N 1/37* (2006.01)
*A61N 1/378* (2006.01)
*A61N 1/372* (2006.01)

(52) U.S. Cl.
CPC ....... *A61N 1/3787* (2013.01); *A61N 1/37217* (2013.01)

(58) Field of Classification Search
CPC .............................. A61N 1/378; A61N 1/3787
See application file for complete search history.

(56) References Cited

U.S. PATENT DOCUMENTS

| | | | |
|---|---|---|---|
| 2,463,533 A | 3/1949 | Harrison et al. |
| 2,967,957 A | 1/1961 | Massa |
| 3,568,661 A | 3/1971 | Franklin |

(Continued)

FOREIGN PATENT DOCUMENTS

| | | |
|---|---|---|
| DE | 3222349 | 1/1984 |
| EP | 0897690 | 8/1997 |

(Continued)

OTHER PUBLICATIONS

Blevins Ph.D. "Formulas for Natural Frequency and Mode Shape" Florida 1979; p. 240; ISBN: 1575241846.

(Continued)

*Primary Examiner* — Eric D. Bertram
(74) *Attorney, Agent, or Firm* — Faegre Baker Daniels LLP

(57) ABSTRACT

An acoustic energy delivery system for delivering acoustic energy to an implantable medical device ("IMD"). The system includes an IMD having a power source and an energy delivery device. The energy delivery device includes a controller and an array of ultrasonic elements electrically coupled to the controller and configured to deliver acoustic energy to the IMD. Methods of delivering acoustic energy to an IMD are also disclosed.

5 Claims, 6 Drawing Sheets

(56) References Cited

U.S. PATENT DOCUMENTS

| | | |
|---|---|---|
| 3,676,720 A | 7/1972 | Libby et al. |
| 3,757,770 A | 9/1973 | Brayshaw et al. |
| 3,792,204 A | 2/1974 | Murayama et al. |
| 3,798,473 A | 3/1974 | Murayama et al. |
| 3,805,796 A | 4/1974 | Terry, Jr. et al. |
| 3,832,580 A | 8/1974 | Yamamuro et al. |
| 3,874,388 A | 4/1975 | King et al. |
| 3,894,198 A | 7/1975 | Murayama et al. |
| 3,940,637 A | 2/1976 | Ohigashi et al. |
| 3,978,353 A | 8/1976 | Kinoshita |
| 4,008,408 A | 2/1977 | Kodama |
| 4,051,455 A | 9/1977 | Fowler |
| 4,056,742 A | 11/1977 | Tibbetts |
| 4,064,375 A | 12/1977 | Russell et al. |
| 4,096,756 A | 6/1978 | Alphonse |
| 4,127,110 A | 11/1978 | Bullara |
| 4,170,742 A | 10/1979 | Itagaki et al. |
| 4,181,864 A | 1/1980 | Etzold |
| 4,227,407 A | 10/1980 | Drost |
| 4,256,115 A | 3/1981 | Bilitch |
| 4,281,484 A | 8/1981 | Massa |
| 4,391,124 A | 7/1983 | Drost et al. |
| 4,407,296 A | 10/1983 | Anderson |
| 4,431,873 A | 2/1984 | Dunn et al. |
| 4,433,400 A | 2/1984 | De Reggi et al. |
| 4,440,983 A | 4/1984 | Facoetti et al. |
| 4,456,850 A | 6/1984 | Inoue et al. |
| 4,471,786 A | 9/1984 | Inagaki et al. |
| 4,481,950 A | 11/1984 | Duggan |
| 4,485,813 A | 12/1984 | Anderson et al. |
| 4,492,107 A | 1/1985 | Sandhu |
| 4,517,665 A | 5/1985 | De Reggi et al. |
| 4,519,401 A | 5/1985 | Ko et al. |
| 4,541,431 A | 9/1985 | Ibrahim et al. |
| 4,558,249 A | 12/1985 | Lerch et al. |
| 4,577,132 A | 3/1986 | Ohigashi et al. |
| 4,580,074 A | 4/1986 | Gilman |
| 4,593,703 A | 6/1986 | Cosman |
| 4,600,855 A | 7/1986 | Strachan |
| 4,642,508 A | 2/1987 | Suzuki et al. |
| 4,653,036 A | 3/1987 | Harris et al. |
| 4,653,508 A | 3/1987 | Cosman |
| 4,660,568 A | 4/1987 | Cosman |
| 4,672,976 A | 6/1987 | Kroll |
| 4,676,255 A | 6/1987 | Cosman |
| 4,677,337 A | 6/1987 | Kleinschmidt et al. |
| 4,781,715 A | 11/1988 | Wurzel |
| 4,793,825 A | 12/1988 | Benjamin et al. |
| 4,835,435 A | 5/1989 | Yeung et al. |
| 4,836,204 A | 6/1989 | Landymore et al. |
| 4,846,191 A | 7/1989 | Brockway et al. |
| 4,886,065 A | 12/1989 | Collins, Jr. |
| 4,900,303 A | 2/1990 | Lemelson |
| 4,911,172 A | 3/1990 | Bui et al. |
| 4,917,089 A | 4/1990 | Sideris |
| 4,940,052 A | 7/1990 | Mann et al. |
| 4,958,100 A | 9/1990 | Crawley et al. |
| 4,966,148 A | 10/1990 | Millar |
| 4,992,692 A | 2/1991 | Dias |
| 5,012,815 A | 5/1991 | Bennett, Jr. et al. |
| 5,024,224 A | 6/1991 | Engebretson |
| 5,040,538 A | 8/1991 | Mortazavi |
| 5,088,576 A | 2/1992 | Potthoff et al. |
| 5,113,859 A | 5/1992 | Funke |
| 5,160,870 A | 11/1992 | Carson et al. |
| 5,178,153 A | 1/1993 | Einzig |
| 5,218,965 A | 6/1993 | Ring |
| 5,283,397 A | 2/1994 | Pavlovic |
| 5,284,138 A | 2/1994 | Kujawski |
| 5,289,821 A | 3/1994 | Swartz |
| 5,300,875 A | 4/1994 | Tuttle |
| 5,303,207 A | 4/1994 | Brady et al. |
| 5,304,206 A | 4/1994 | Baker, Jr. et al. |
| 5,314,457 A | 5/1994 | Jeutter et al. |
| 5,334,217 A | 8/1994 | Das |
| 5,339,290 A | 8/1994 | Greenstein |
| 5,367,500 A | 11/1994 | Ng |
| 5,381,067 A | 1/1995 | Greenstein et al. |
| 5,381,386 A | 1/1995 | Lum et al. |
| 5,410,587 A | 4/1995 | Grunwell |
| 5,411,551 A | 5/1995 | Winston et al. |
| 5,415,630 A | 5/1995 | Gory et al. |
| 5,423,334 A | 6/1995 | Jordan |
| 5,433,736 A | 7/1995 | Nilsson |
| 5,438,553 A | 8/1995 | Wilson et al. |
| 5,438,554 A | 8/1995 | Seyed-Bolorforosh et al. |
| 5,451,235 A | 9/1995 | Lock et al. |
| 5,476,488 A | 12/1995 | Morgan et al. |
| 5,483,501 A | 1/1996 | Park et al. |
| 5,488,954 A | 2/1996 | Sleva et al. |
| 5,495,137 A | 2/1996 | Park et al. |
| 5,507,786 A | 4/1996 | Morgan et al. |
| 5,509,900 A | 4/1996 | Kirkman |
| 5,554,177 A | 9/1996 | Kieval et al. |
| 5,562,714 A | 10/1996 | Grevious |
| 5,571,152 A | 11/1996 | Chen et al. |
| 5,601,600 A | 2/1997 | Ton |
| 5,604,531 A | 2/1997 | Iddan et al. |
| 5,628,782 A | 5/1997 | Myers |
| 5,634,936 A | 6/1997 | Linden et al. |
| 5,656,036 A | 8/1997 | Palmaz |
| 5,662,711 A | 9/1997 | Douglas |
| 5,679,026 A | 10/1997 | Fain et al. |
| 5,704,352 A | 1/1998 | Tremblay et al. |
| 5,725,552 A | 3/1998 | Kotula et al. |
| 5,733,249 A | 3/1998 | Katzin et al. |
| 5,733,294 A | 3/1998 | Forber et al. |
| 5,733,313 A | 3/1998 | Barreras et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,757,104 A | 5/1998 | Getman et al. |
| 5,772,669 A | 6/1998 | Vrba |
| 5,775,331 A | 7/1998 | Raymond et al. |
| 5,776,168 A | 7/1998 | Gunderson |
| 5,776,178 A | 7/1998 | Pohndorf et al. |
| 5,792,195 A | 8/1998 | Carlson et al. |
| 5,800,497 A | 9/1998 | Bakels et al. |
| 5,807,258 A | 9/1998 | Cimochowski et al. |
| 5,824,053 A | 10/1998 | Khosravi et al. |
| 5,825,117 A | 10/1998 | Ossmann et al. |
| 5,832,924 A | 11/1998 | Archibald et al. |
| 5,833,603 A | 11/1998 | Kovacs et al. |
| 5,843,135 A | 12/1998 | Weijand et al. |
| 5,855,563 A | 1/1999 | Kaplan et al. |
| 5,860,923 A | 1/1999 | Lenker et al. |
| 5,870,351 A | 2/1999 | Ladabaum et al. |
| 5,873,835 A | 2/1999 | Hastings et al. |
| 5,879,283 A | 3/1999 | Adams et al. |
| 5,891,154 A | 4/1999 | Loeffler |
| 5,935,081 A | 8/1999 | Kadhiresan |
| 5,956,292 A | 9/1999 | Bernstein |
| 5,957,950 A | 9/1999 | Mockros et al. |
| 5,967,980 A | 10/1999 | Ferre et al. |
| 5,967,986 A | 10/1999 | Cimochowski et al. |
| 5,967,989 A | 10/1999 | Cimochowski et al. |
| 5,995,876 A | 11/1999 | Kruse et al. |
| 6,002,969 A | 12/1999 | Machek et al. |
| 6,015,386 A | 1/2000 | Kensey et al. |
| 6,015,387 A | 1/2000 | Schwartz et al. |
| 6,030,413 A | 2/2000 | Lazarus |
| 6,033,366 A | 3/2000 | Brockway et al. |
| 6,044,298 A | 3/2000 | Salo et al. |
| 6,053,873 A | 4/2000 | Govari et al. |
| 6,056,775 A | 5/2000 | Borghi et al. |
| 6,058,329 A | 5/2000 | Salo et al. |
| 6,068,589 A | 5/2000 | Neukermans |
| 6,076,016 A | 6/2000 | Feierbach |
| 6,077,227 A | 6/2000 | Miesel et al. |
| 6,082,367 A | 7/2000 | Greeninger et al. |
| 6,097,984 A | 8/2000 | Douglas |
| 6,106,464 A | 8/2000 | Bass et al. |
| 6,140,740 A | 10/2000 | Porat et al. |
| 6,141,588 A | 10/2000 | Cox et al. |

(56) References Cited

U.S. PATENT DOCUMENTS

| | | |
|---|---|---|
| 6,159,156 A | 12/2000 | Van Bockel |
| 6,179,858 B1 | 1/2001 | Squire et al. |
| 6,185,452 B1 | 2/2001 | Schulman et al. |
| 6,193,745 B1 | 2/2001 | Fogarty et al. |
| 6,214,025 B1 | 4/2001 | Thistle et al. |
| 6,223,081 B1 | 4/2001 | Kerver |
| 6,231,516 B1 | 5/2001 | Keilman et al. |
| 6,236,889 B1 | 5/2001 | Soykan et al. |
| 6,239,724 B1 | 5/2001 | Doron et al. |
| 6,240,312 B1 | 5/2001 | Alfano et al. |
| 6,246,898 B1 | 6/2001 | Vesely et al. |
| 6,277,078 B1 | 8/2001 | Porat et al. |
| 6,278,790 B1 | 8/2001 | Davis et al. |
| 6,309,350 B1 | 10/2001 | VanTassel et al. |
| 6,328,669 B1 | 12/2001 | Imanishi et al. |
| 6,328,699 B1 | 12/2001 | Eigler et al. |
| 6,331,163 B1 | 12/2001 | Kaplan |
| 6,353,277 B1 | 3/2002 | Hahn-Jose |
| 6,379,308 B1 | 4/2002 | Brockway et al. |
| 6,409,674 B1 | 6/2002 | Brockway et al. |
| 6,409,675 B1 | 6/2002 | Turcott |
| 6,416,474 B1 | 7/2002 | Penner et al. |
| 6,432,050 B1 | 8/2002 | Porat et al. |
| 6,442,413 B1 | 8/2002 | Silver |
| 6,447,522 B2 | 9/2002 | Gambale et al. |
| 6,472,991 B1 | 10/2002 | Schulman et al. |
| 6,475,170 B1 | 11/2002 | Doron et al. |
| 6,477,406 B1 | 11/2002 | Turcott |
| 6,480,733 B1 | 11/2002 | Turcott |
| 6,486,588 B2 | 11/2002 | Doron et al. |
| 6,504,286 B1 | 1/2003 | Porat et al. |
| 6,504,289 B2 | 1/2003 | Toda et al. |
| 6,522,926 B1 | 2/2003 | Kieval et al. |
| 6,527,729 B1 | 3/2003 | Turcott |
| 6,527,780 B1 | 3/2003 | Wallace et al. |
| 6,537,200 B2 | 3/2003 | Leysieffer et al. |
| 6,543,272 B1 | 4/2003 | Vitek |
| 6,554,761 B1 | 4/2003 | Puria et al. |
| 6,575,894 B2 | 6/2003 | Leysieffer et al. |
| 6,585,763 B1 | 7/2003 | Keilman et al. |
| 6,592,553 B2 | 7/2003 | Zhang et al. |
| 6,600,949 B1 | 7/2003 | Turcott |
| 6,628,989 B1 * | 9/2003 | Penner et al. ............ 607/59 |
| 6,629,922 B1 | 10/2003 | Puria et al. |
| 6,629,951 B2 | 10/2003 | Laufer et al. |
| 6,643,548 B1 | 11/2003 | Mai et al. |
| 6,645,143 B2 | 11/2003 | VanTassel et al. |
| 6,645,145 B1 | 11/2003 | Dreschel et al. |
| 6,654,638 B1 | 11/2003 | Sweeney |
| 6,660,021 B1 | 12/2003 | Palmer et al. |
| 6,671,550 B2 | 12/2003 | Iaizzo et al. |
| 6,685,638 B1 | 2/2004 | Taylor et al. |
| 6,689,056 B1 | 2/2004 | Kilcoyne et al. |
| 6,697,674 B2 | 2/2004 | Leysieffer |
| 6,699,186 B1 | 3/2004 | Wolinsky et al. |
| 6,702,847 B2 | 3/2004 | DiCarlo |
| 6,720,709 B2 | 4/2004 | Porat et al. |
| 6,730,108 B2 | 5/2004 | Van Tassel et al. |
| 6,738,671 B2 | 5/2004 | Christophersom et al. |
| 6,740,076 B2 | 5/2004 | Hoben et al. |
| 6,741,714 B2 | 5/2004 | Jensen |
| 6,743,173 B2 | 6/2004 | Penner et al. |
| 6,746,404 B2 | 6/2004 | Schwartz |
| 6,747,916 B1 | 6/2004 | Fleury et al. |
| 6,755,855 B2 | 6/2004 | Yurek et al. |
| 6,763,722 B2 | 7/2004 | Fjield et al. |
| 6,764,446 B2 | 7/2004 | Wolinsky et al. |
| 6,772,490 B2 | 8/2004 | Toda |
| 6,783,499 B2 | 8/2004 | Schwartz |
| 6,792,308 B2 | 9/2004 | Corbucci |
| 6,800,060 B2 | 10/2004 | Marshall |
| 6,840,956 B1 | 1/2005 | Wolinsky et al. |
| 6,855,115 B2 | 2/2005 | Fonseca et al. |
| 6,868,288 B2 | 3/2005 | Thompson |
| 6,890,303 B2 | 5/2005 | Fitz |
| 6,899,729 B1 | 5/2005 | Cox et al. |
| 6,904,308 B2 | 6/2005 | Frisch et al. |
| 6,920,347 B2 | 7/2005 | Simon et al. |
| 6,926,670 B2 | 8/2005 | Rich et al. |
| 6,934,573 B1 | 8/2005 | Glukhovsky et al. |
| 6,950,690 B1 | 9/2005 | Meron et al. |
| 6,958,034 B2 | 10/2005 | Iddan |
| 6,970,742 B2 | 11/2005 | Mann et al. |
| 6,972,017 B2 | 12/2005 | Smith et al. |
| 6,984,205 B2 | 1/2006 | Gazdzinski |
| 6,999,685 B1 | 2/2006 | Kawase et al. |
| 7,001,329 B2 | 2/2006 | Kobayashi et al. |
| 7,006,858 B2 | 2/2006 | Silver et al. |
| 7,009,634 B2 | 3/2006 | Iddan et al. |
| 7,011,671 B2 | 3/2006 | Welch |
| 7,015,392 B1 | 3/2006 | Dickenson |
| 7,016,739 B2 | 3/2006 | Bange et al. |
| 7,024,248 B2 | 4/2006 | Penner |
| 7,033,322 B2 | 4/2006 | Silver |
| 7,035,684 B2 | 4/2006 | Lee |
| 7,039,453 B2 | 5/2006 | Mullick et al. |
| 7,060,038 B2 | 6/2006 | Letort et al. |
| 7,064,472 B2 | 6/2006 | Pelrine et al. |
| 7,065,409 B2 | 6/2006 | Mazar |
| 7,065,709 B2 | 6/2006 | Ellis et al. |
| 7,076,305 B2 | 7/2006 | Imran et al. |
| 7,083,822 B2 | 8/2006 | Brightbill |
| 7,107,103 B2 | 9/2006 | Schulman et al. |
| 7,114,502 B2 | 10/2006 | Schulman et al. |
| 7,115,096 B2 | 10/2006 | Siejko et al. |
| 7,116,352 B2 | 10/2006 | Yaron |
| 7,118,529 B2 | 10/2006 | Glukhovsky et al. |
| 7,118,531 B2 | 10/2006 | Krill |
| 7,123,962 B2 | 10/2006 | Siejko et al. |
| 7,127,290 B2 | 10/2006 | Girouard et al. |
| 7,131,986 B2 | 11/2006 | Sirhan et al. |
| 7,160,258 B2 | 1/2007 | Imran et al. |
| 7,176,602 B2 | 2/2007 | Schlenke |
| 7,181,261 B2 | 2/2007 | Silver et al. |
| 7,198,603 B2 | 4/2007 | Penner et al. |
| 7,211,045 B2 | 5/2007 | Dala-Krishna et al. |
| 7,220,232 B2 | 5/2007 | Suorsa et al. |
| 7,228,175 B2 | 6/2007 | Jain et al. |
| 7,236,821 B2 | 6/2007 | Cates et al. |
| 7,248,923 B2 | 7/2007 | Maile et al. |
| 7,260,429 B2 | 8/2007 | Siejko et al. |
| 7,273,457 B2 | 9/2007 | Penner |
| 7,283,874 B2 | 10/2007 | Penner |
| 7,308,319 B2 | 12/2007 | Lovett et al. |
| 7,335,169 B2 | 2/2008 | Thompson et al. |
| 7,338,512 B2 | 3/2008 | McGuckin, Jr. et al. |
| 7,347,868 B2 | 3/2008 | Burnett et al. |
| 7,392,094 B2 | 6/2008 | Zhang et al. |
| 7,431,699 B2 | 10/2008 | Siejko et al. |
| 7,437,193 B2 | 10/2008 | Parramon et al. |
| 7,452,334 B2 | 11/2008 | Gianchandani et al. |
| 7,477,946 B2 | 1/2009 | Tockman et al. |
| 7,522,962 B1 | 4/2009 | Doran et al. |
| 7,555,351 B2 | 6/2009 | Zhang et al. |
| 7,570,998 B2 | 8/2009 | Zhang et al. |
| 7,572,228 B2 | 8/2009 | Wolinsky et al. |
| 7,580,750 B2 | 8/2009 | Doron et al. |
| 7,615,012 B2 | 11/2009 | Von Arx et al. |
| 7,634,318 B2 * | 12/2009 | Tran et al. ............ 607/61 |
| 7,655,022 B2 | 2/2010 | Simpson et al. |
| 7,744,542 B2 | 6/2010 | Piaget et al. |
| 7,780,694 B2 | 8/2010 | Palmer et al. |
| 7,801,626 B2 | 9/2010 | Moser |
| 7,850,708 B2 | 12/2010 | Pal |
| 7,890,188 B2 | 2/2011 | Zhang et al. |
| 7,912,548 B2 | 3/2011 | Mi et al. |
| 7,930,031 B2 | 4/2011 | Penner |
| 7,948,148 B2 | 5/2011 | Porat et al. |
| 7,949,396 B2 | 5/2011 | Mi et al. |
| 8,057,399 B2 | 11/2011 | Greenland et al. |
| 8,060,214 B2 | 11/2011 | Larson et al. |
| 8,204,599 B2 | 6/2012 | Liao et al. |
| 8,271,093 B2 | 9/2012 | Von Arx et al. |
| 8,277,441 B2 | 10/2012 | Porat et al. |

(56) References Cited

U.S. PATENT DOCUMENTS

| | | | |
|---|---|---|---|
| 8,340,778 B2 * | 12/2012 | Tran et al. | 607/61 |
| 8,577,460 B2 | 11/2013 | Penner | |
| 8,676,349 B2 | 3/2014 | Stalker et al. | |
| 8,934,972 B2 | 1/2015 | Penner | |
| 9,026,229 B2 | 5/2015 | Stalker et al. | |
| 9,149,193 B2 | 10/2015 | Wolinsky et al. | |
| 2001/0026111 A1 | 10/2001 | Doran et al. | |
| 2002/0038135 A1 | 3/2002 | Connelly et al. | |
| 2002/0045920 A1 | 4/2002 | Thompson | |
| 2002/0045921 A1 | 4/2002 | Wolinsky et al. | |
| 2002/0062143 A1 | 5/2002 | Baudino et al. | |
| 2002/0077555 A1 | 6/2002 | Schwartz | |
| 2002/0077673 A1 * | 6/2002 | Penner | A61B 5/00 607/60 |
| 2002/0123672 A1 | 9/2002 | Christophersom et al. | |
| 2002/0151816 A1 | 10/2002 | Rich et al. | |
| 2002/0165601 A1 | 11/2002 | Clerc | |
| 2002/0169584 A1 | 11/2002 | Fu et al. | |
| 2002/0177782 A1 | 11/2002 | Penner | |
| 2002/0183628 A1 | 12/2002 | Reich et al. | |
| 2002/0188207 A1 | 12/2002 | Richter | |
| 2003/0006673 A1 | 1/2003 | Porat et al. | |
| 2003/0014080 A1 | 1/2003 | Baudino | |
| 2003/0036746 A1 | 2/2003 | Penner et al. | |
| 2003/0036755 A1 | 2/2003 | Ginn | |
| 2003/0114897 A1 | 6/2003 | Von Arx et al. | |
| 2003/0139796 A1 | 7/2003 | Sequin et al. | |
| 2003/0195606 A1 | 10/2003 | Davidson et al. | |
| 2003/0200031 A1 | 10/2003 | Kok | |
| 2003/0233095 A1 | 12/2003 | Urbanski et al. | |
| 2004/0006377 A1 | 1/2004 | Behm | |
| 2004/0054403 A1 | 3/2004 | Israel | |
| 2004/0106954 A1 | 6/2004 | Whitehurst et al. | |
| 2004/0116992 A1 | 6/2004 | Wardle et al. | |
| 2004/0122484 A1 | 6/2004 | Hatlestad et al. | |
| 2004/0127792 A1 | 7/2004 | Siejko et al. | |
| 2004/0138572 A1 | 7/2004 | Thiagarajan | |
| 2004/0147969 A1 | 7/2004 | Mann et al. | |
| 2004/0172079 A1 | 9/2004 | Chinchoy | |
| 2004/0176672 A1 | 9/2004 | Silver et al. | |
| 2004/0204744 A1 | 10/2004 | Penner et al. | |
| 2004/0215228 A1 | 10/2004 | Simpson et al. | |
| 2004/0230249 A1 | 11/2004 | Haefner | |
| 2004/0260214 A1 | 12/2004 | Echt et al. | |
| 2005/0080472 A1 | 4/2005 | Atkinson et al. | |
| 2005/0096702 A1 | 5/2005 | Denker et al. | |
| 2005/0109338 A1 | 5/2005 | Stahmann et al. | |
| 2005/0115561 A1 | 6/2005 | Stahmann et al. | |
| 2005/0124875 A1 | 6/2005 | Kawano et al. | |
| 2005/0131472 A1 | 6/2005 | Ding et al. | |
| 2005/0136385 A1 | 6/2005 | Mann et al. | |
| 2005/0137490 A1 | 6/2005 | Scheiner et al. | |
| 2005/0149108 A1 | 7/2005 | Cox | |
| 2005/0149128 A1 | 7/2005 | Heil et al. | |
| 2005/0149138 A1 | 7/2005 | Min et al. | |
| 2005/0149155 A1 | 7/2005 | Scheiner et al. | |
| 2005/0149156 A1 | 7/2005 | Libbus et al. | |
| 2005/0154321 A1 | 7/2005 | Wolinsky et al. | |
| 2005/0165456 A1 | 7/2005 | Mann et al. | |
| 2005/0182387 A1 | 8/2005 | Webler | |
| 2005/0203444 A1 | 9/2005 | Schonenberger et al. | |
| 2005/0209678 A1 | 9/2005 | Henkes et al. | |
| 2005/0245840 A1 | 11/2005 | Christopherson et al. | |
| 2005/0265999 A1 | 12/2005 | Bush et al. | |
| 2006/0004290 A1 | 1/2006 | Smith et al. | |
| 2006/0009818 A1 | 1/2006 | Von Arx et al. | |
| 2006/0047205 A1 | 3/2006 | Ludomirsky et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0079740 A1 | 4/2006 | Silver et al. | |
| 2006/0089627 A1 | 4/2006 | Burnett et al. | |
| 2006/0089694 A1 | 4/2006 | Zhang et al. | |
| 2006/0122522 A1 | 6/2006 | Chavan et al. | |
| 2006/0136004 A1 * | 6/2006 | Cowan et al. | 607/33 |
| 2006/0142819 A1 | 6/2006 | Penner et al. | |
| 2006/0149329 A1 | 7/2006 | Penner | |
| 2006/0149330 A1 | 7/2006 | Mann et al. | |
| 2006/0178586 A1 | 8/2006 | Dobak | |
| 2006/0206153 A1 | 9/2006 | Libbus et al. | |
| 2006/0241735 A1 | 10/2006 | Tockman et al. | |
| 2006/0259085 A1 | 11/2006 | Zhang et al. | |
| 2006/0287700 A1 | 12/2006 | White et al. | |
| 2006/0293741 A1 | 12/2006 | Johnson et al. | |
| 2007/0049833 A1 | 3/2007 | Tearney et al. | |
| 2007/0049977 A1 | 3/2007 | Von Arx et al. | |
| 2007/0055184 A1 | 3/2007 | Echt et al. | |
| 2007/0055313 A1 | 3/2007 | Stahmann et al. | |
| 2007/0060959 A1 | 3/2007 | Salo et al. | |
| 2007/0093875 A1 | 4/2007 | Chavan et al. | |
| 2007/0129637 A1 | 6/2007 | Wolinsky et al. | |
| 2007/0142728 A1 | 6/2007 | Penner | |
| 2007/0156126 A1 | 7/2007 | Flaherty | |
| 2007/0156205 A1 | 7/2007 | Larson et al. | |
| 2007/0162090 A1 | 7/2007 | Penner | |
| 2007/0179583 A1 | 8/2007 | Goetzinger et al. | |
| 2007/0191904 A1 | 8/2007 | Libbus et al. | |
| 2007/0208390 A1 | 9/2007 | Von Arx et al. | |
| 2007/0247565 A1 | 10/2007 | Sasaki et al. | |
| 2007/0250126 A1 | 10/2007 | Maile et al. | |
| 2007/0274565 A1 | 11/2007 | Penner | |
| 2007/0282413 A1 | 12/2007 | Tockman et al. | |
| 2007/0282415 A1 | 12/2007 | Tockman et al. | |
| 2008/0021289 A1 | 1/2008 | Zhang et al. | |
| 2008/0021509 A1 | 1/2008 | Mi et al. | |
| 2008/0021510 A1 | 1/2008 | Mi et al. | |
| 2008/0033497 A1 | 2/2008 | Bulkes et al. | |
| 2008/0071178 A1 | 3/2008 | Greenland et al. | |
| 2008/0071248 A1 | 3/2008 | Delgado et al. | |
| 2008/0071339 A1 | 3/2008 | Stalker et al. | |
| 2008/0108904 A1 | 5/2008 | Heil | |
| 2008/0154135 A1 | 6/2008 | Kimura et al. | |
| 2008/0176271 A1 | 7/2008 | Silver et al. | |
| 2008/0195186 A1 | 8/2008 | Li et al. | |
| 2008/0243007 A1 | 10/2008 | Liao et al. | |
| 2008/0275350 A1 | 11/2008 | Liao et al. | |
| 2008/0283066 A1 | 11/2008 | Delgado et al. | |
| 2008/0294208 A1 * | 11/2008 | Willis et al. | 607/3 |
| 2008/0312720 A1 | 12/2008 | Tran et al. | |
| 2009/0054793 A1 | 2/2009 | Nunez et al. | |
| 2009/0270742 A1 | 10/2009 | Wolinsky et al. | |
| 2010/0004718 A1 | 1/2010 | Doran et al. | |
| 2010/0049269 A1 | 2/2010 | Tran | |
| 2010/0094105 A1 | 4/2010 | Porat et al. | |
| 2010/0274302 A1 | 10/2010 | Armstrong et al. | |
| 2011/0178578 A1 | 7/2011 | Porat et al. | |
| 2011/0190669 A1 | 8/2011 | Mi et al. | |
| 2012/0327747 A1 | 12/2012 | Porat et al. | |
| 2015/0201848 A1 | 7/2015 | Stalker et al. | |

FOREIGN PATENT DOCUMENTS

| | | |
|---|---|---|
| EP | 0798016 | 10/1997 |
| EP | 0897690 B1 | 2/1999 |
| EP | 0928598 A2 | 7/1999 |
| EP | 1068836 A2 | 1/2001 |
| EP | 1151719 | 4/2001 |
| EP | 1422970 | 5/2004 |
| EP | 1488735 B1 | 6/2007 |
| EP | 2162185 B1 | 7/2015 |
| GB | 2333044 A | 7/1999 |
| JP | 57-177735 | 11/1982 |
| JP | 60-216697 | 10/1985 |
| JP | 62-073900 | 4/1987 |
| JP | 62-102734 | 5/1987 |
| JP | 05-023323 | 2/1993 |
| JP | 05-284599 | 10/1993 |
| JP | 07-046694 | 2/1995 |
| JP | 07-301670 | 11/1995 |
| JP | 08-331065 | 12/1996 |
| JP | 09-147284 | 6/1997 |
| JP | 09-225042 | 9/1997 |
| JP | 09-237398 | 9/1997 |

(56) References Cited

FOREIGN PATENT DOCUMENTS

| | | |
|---|---|---|
| JP | 10-093477 | 4/1998 |
| JP | 2000507142 A | 9/1998 |
| JP | 10-294995 | 11/1998 |
| JP | H11089942 A | 4/1999 |
| JP | 2000-334048 | 12/2000 |
| JP | 2001061790 A | 3/2001 |
| JP | 2001-514455 | 9/2001 |
| JP | 2002-508682 | 3/2002 |
| JP | 2002515807 A | 5/2002 |
| JP | 2002-528887 | 9/2002 |
| JP | 2003-079621 | 3/2003 |
| JP | 2003-519542 | 6/2003 |
| JP | 2003-218805 | 7/2003 |
| JP | 2004041724 A | 2/2004 |
| JP | 2004-147319 | 5/2004 |
| JP | 2006-015137 | 1/2006 |
| JP | 2006500991 A | 1/2006 |
| JP | 2006-166985 | 6/2006 |
| RU | 2239383 | 11/2004 |
| WO | 8303348 A1 | 10/1983 |
| WO | WO 83/03345 | 10/1983 |
| WO | WO 97/01986 | 1/1997 |
| WO | WO 97/33513 | 9/1997 |
| WO | WO 97/35636 | 10/1997 |
| WO | WO 97/47236 | 12/1997 |
| WO | WO 98/26716 | 6/1998 |
| WO | WO 98/29030 | 7/1998 |
| WO | WO 98/51025 | 11/1998 |
| WO | WO 98/52142 | 11/1998 |
| WO | WO 98/52641 | 11/1998 |
| WO | WO 99/04287 | 1/1999 |
| WO | WO 99/26530 | 6/1999 |
| WO | WO 99/34453 | 7/1999 |
| WO | WO9934453 A1 | 7/1999 |
| WO | WO9934731 A1 | 7/1999 |
| WO | WO 99/59460 | 11/1999 |
| WO | 0016686 A2 | 3/2000 |
| WO | WO 00/16686 | 3/2000 |
| WO | 0059376 A1 | 10/2000 |
| WO | WO 01/51123 | 7/2001 |
| WO | 0167989 A2 | 9/2001 |
| WO | 0176687 A2 | 10/2001 |
| WO | WO0174278 A2 | 10/2001 |
| WO | 0187137 A2 | 11/2001 |
| WO | WO 03/068047 | 8/2003 |
| WO | 2004024034 A8 | 1/2004 |
| WO | WO 2004/091719 | 10/2004 |
| WO | 2004110263 A1 | 12/2004 |
| WO | 2005058202 A1 | 6/2005 |
| WO | 2005066849 A2 | 7/2005 |
| WO | 2005067817 A1 | 7/2005 |
| WO | WO 2006/010010 | 1/2006 |
| WO | 2006062725 A1 | 6/2006 |
| WO | WO 2006/056857 | 6/2006 |
| WO | WO 2006/069215 | 6/2006 |
| WO | WO 2007/025163 | 3/2007 |
| WO | WO 2007/047966 | 4/2007 |
| WO | 2007057739 A1 | 5/2007 |
| WO | 2007062299 A2 | 5/2007 |
| WO | 2007082115 A2 | 7/2007 |
| WO | 2008002654 A2 | 1/2008 |
| WO | WO 2008/011570 | 1/2008 |
| WO | WO 2008/011577 | 1/2008 |
| WO | 2008034077 A2 | 3/2008 |
| WO | 2008057720 A1 | 5/2008 |
| WO | WO2008060197 A1 | 5/2008 |
| WO | 2008144191 A2 | 11/2008 |

OTHER PUBLICATIONS

C. Hierold et al. (Germany 1998) "Implantable Low Power Integrated Pressure Sensor System for Minimal Invasive Telemetric Patient Monitoring" IEEE pp. 568-573.

Cassereau et al. "Time Reversal of Ultrasonic Fields Part 3: Theory of the Closed TimeReversal Cavity" IEEE Transactions on Ultrasonics Ferroelectrics and Frequency Control vol. 39 No. 5, Sep. 1992 pp. 579-592.

ER. Cosman et al. (Massachussetts Apr. 1979) "A Telemetric Pressure Sensor for Ventricular Shunt Systems" Surgical Neurology vol. 11 No. 4, pp. 287-294.

Fink et al. "Time Reversal Acoustics" 2004 IEEE Transactions on Ultrasonics Ferroelectrics and Frequency Control Joint 50th Anniversary Conference Ultrasonics Symposium pp. 850-859.

Fink "Time Reversal of Ultrasonic Fields Part 1: Basic Principles" IEEE Transactions on Ultrasonics Ferroelectrics and Frequency Control vol. 39 No. 5, Sep. 1992, pp. 555-566.

G. W. H. Schurink et al. (1998) "Late Endoleak after Endovascular Therapy for Abdominal Aortic Aneurysm" Eur. J. Vasc. Endovasc. Surg. vol. 17, pp. 448-450.

GH White et al. (1997) "Endoleak Following Endoluminal Repair of AAA: Management Options and Patient Outcomes" J. Endovasc Surg. p. I45.

Karl E. Richard et al. (Germany Jan. 1999) "First clinical results with a telemetric shunt-integrated ICP-sensor" Neurological Research vol. 21, pp. 117-120.

Prof. Dr. Johannes Zacheja et al. (Germany Sep. 1996) "An Implantable Microsystem for Biomedical Applications" Micro System Technologies 96 pp. 717-722.

S. K. Gupta et al. (1999) "Use of a Piezoelectric Film Sensor for Monitoring Vascular Grafts" The American Journal of Surgery vol. 160, pp. 182-186.

T. Chuter et al. (Sweden Jan. 1997) "Aneurysm Pressure following Endovascular Exclusion" Eur. J. Vasc. Endovasc. Surg. vol. 13, pp. 85-87.

T.A. Cochran et al. (1990) "Aortic Aneurysm Abdominal" Current Therapy in Adult Medicine Fourth Edition, pp. 509-517.

Wu et al. "Time Reversal of Ultrasonic Fields Part 2: Experimental Results" IEEE Transactions on Ultrasonics Ferroelectrics and Frequency Control vol. 39 No. 5, Sep. 1992, pp. 567-578.

Z. Tang et al. (May 1995) "Data Transmission from an Implantable Biotelemeter by LoadShift Keying Using Circuit Configuration Modulator" IEEE Transactions on Biomedical Engineering vol. 42 No. 5, pp. 524-528.

International Search Report and Written Opinion issued in PT/US2007/073998, mailed Mar. 6, 2008, 15 pages.

International Search Report and Written Opinion issued in PCT/US2008/064994, mailed Dec. 22, 2008, 17 pages.

Goodall, Eleanor V. et al., "Position-Seletive Activation of Peripheral Nerve Fibers with a Cuff Electrode", IEEE Transactions on Biomedical Engineering, IEEE Service Center, Piscataway, NJ, US, vol. 43, No. 8, Aug. 1, 1996.

Holmes et al. "SirolimusEluting Stents vs. Vascular Brachytherapy for InStent Restenosis Within BareMetal Stents" JAMA295 (11): 1264-1273 Mar. 15, 2006.

International Search Report and Written Opinion from PCT/US2008/062229, mailed Jan. 5, 2009 7pages.

International Search Report and Written Opinion issued in PCT/US2010/020756, mailed Sep. 27, 2010.

Invitation to Pay Fees and Partial Search Report issued in PCT/US2010/020756, mailed May 12, 2010.

Lanning & Shandas, "Development and Validation of Implantable Sensors for Monitoring Function of Prosthetic Heart Valves: In Vitro Studies", Medical & Biological Engineering & Computing, Jul. 2003, vol. 41, issue 4, pp. 416-424.

Mullins, C.E. et al., "Implantation of Balloon-Expandable Intravascular Grafts by Catheterization in Pulmonary Arteries and Systemic Veins", Circulation, 1988, vol. 77, pp. 188-199.

Sheth et al. "Subacute Thrombosis and Vascular Injury Resulting From Slotted-Tube Nitinol and Stainless Steel Stents in a Rabbit Carotid Artery Model" Circulation 1996, 94: 1733-1740.

Stone et al, "Paclitaxel-Eluting Stents vs. Vascular Brachytherapy for In-Stent Restenosis Within Bare-Metal Stents" JAMA 295(11): 1253-1263, Mar. 15, 2006.

Triantaphyllou, Evangelos et al., "Development and Evaluation of Five Fuzzy Multiattribute Decision-Making Methods", International Journal of Approximate Reasoning 1996; 14:281-310.

(56) References Cited

OTHER PUBLICATIONS

Wenaweser et al. "Stent thrombosis following baremetal stent implantation: success of emergency percutaneous coronary intervention and predictors of adverse outcome" European Heart Journal 26: 1180-1187 2005.

* cited by examiner

MULTI-ELEMENT ACOUSTIC RECHARGING SYSTEM

CROSS-REFERENCE TO RELATED APPLICATIONS

This application is a continuation of U.S. application Ser. No. 12/611,686, filed Nov. 3, 2009, now U.S. Pat. No. 8,340,778, which is a continuation of U.S. application Ser. No. 12/128,396, filed May 28, 2008, now U.S. Pat. No. 7,634,318, which claims priority under 35 U.S.C. §119 to U.S. Provisional Application No. 60/943,939, filed Jun. 14, 2007, entitled "Multi-Element Acoustic Recharging System," all of which are incorporated herein by reference in their entirety for all purposes.

TECHNICAL FIELD

The present invention relates to implantable medical devices and methods of delivering energy to implantable medical devices. More specifically, the invention relates to devices and methods used to deliver energy to an implantable medical device using a device located external to a patient's body.

BACKGROUND

Implantable medical devices are used to treat a variety of medical conditions. Examples of implantable medical devices include drug delivery devices, pain management devices, and devices that treat heart rhythm disorders. Examples of implantable medical devices that treat heart rhythm disorders are cardiac pacemakers, implantable cardioverter defibrillators, and cardiac resynchronization therapy ("CRT") devices. A cardiac pacemaker is commonly used to treat bradycardia. An implantable cardioverter defibrillator ("ICD") is commonly used to treat tachycardia. A CRT device is commonly used to treat heart failure associated dyssynchrony. These devices generally include a pulse generator and one or more leads that deliver electrical energy to the heart. The pulse generator typically includes a housing for a battery and electrical circuitry and a header for connecting the leads to the pulse generator. Other examples of implantable medical devices include remote devices with sensing, monitoring and/or stimulating functions. For example, implantable pressure sensors can be located in the vasculature and used in conjunction with pacemakers, CRT devices, and ICDs.

At some point, the battery or power source within an implantable medical device runs out of energy. Generally, this energy depletion requires replacement of the implantable medical device. These devices, and others, may include a rechargeable power source to extend their usable lifetime. Due to the nature of implantable medical devices, methods for recharging are typically indirect, utilizing an external device not physically connected to the implantable medical device. One method of recharging the power source of an implantable medical device is by the conversion of acoustic energy to electrical energy. Using ultrasonic transducers, for example, acoustic energy can be transmitted through the body to the implantable medical device for recharging the electrical power source. Current technologies for acoustically charging a power source of an implantable medical device, however, are sometimes inefficient. Thus, there is a need for an improved device and method for delivering acoustic energy to implantable medical devices.

SUMMARY

In one embodiment, the invention is an acoustic energy delivery system for delivering acoustic energy to an implantable medical device ("IMD"). The system comprises an acoustic energy delivery device and an IMD. The acoustic energy delivery device includes a power source, a controller, and a multi-element array of ultrasonic elements configured to deliver acoustic energy through the body to the IMD. In some embodiments, the IMD includes an energizable power source and an acoustic transducer to receive acoustic energy delivered by the energy delivery device. In use, the controller is configured to selectively control one or more of the ultrasonic elements within the array to manipulate the delivery of acoustic energy through the body.

In another embodiment, the invention includes a method of controlling an energy delivery device for delivering acoustic energy to an IMD. In one embodiment, the method comprises sending one or more signals to an IMD and processing one or more responsive signals sent by the IMD. The energy delivery device is configured to operate based upon the responsive signals received from the IMD. An array of ultrasonic elements is electrically coupled to a controller, allowing the controller to control the excitation of each transducer element or subsets of transducer elements to more effectively deliver acoustic energy to the IMD. In some embodiments, the one or more signals sent to the IMD causes the IMD to enter into a charging mode and send out a plurality of test pulses to an energy delivery device having an array of ultrasonic elements.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
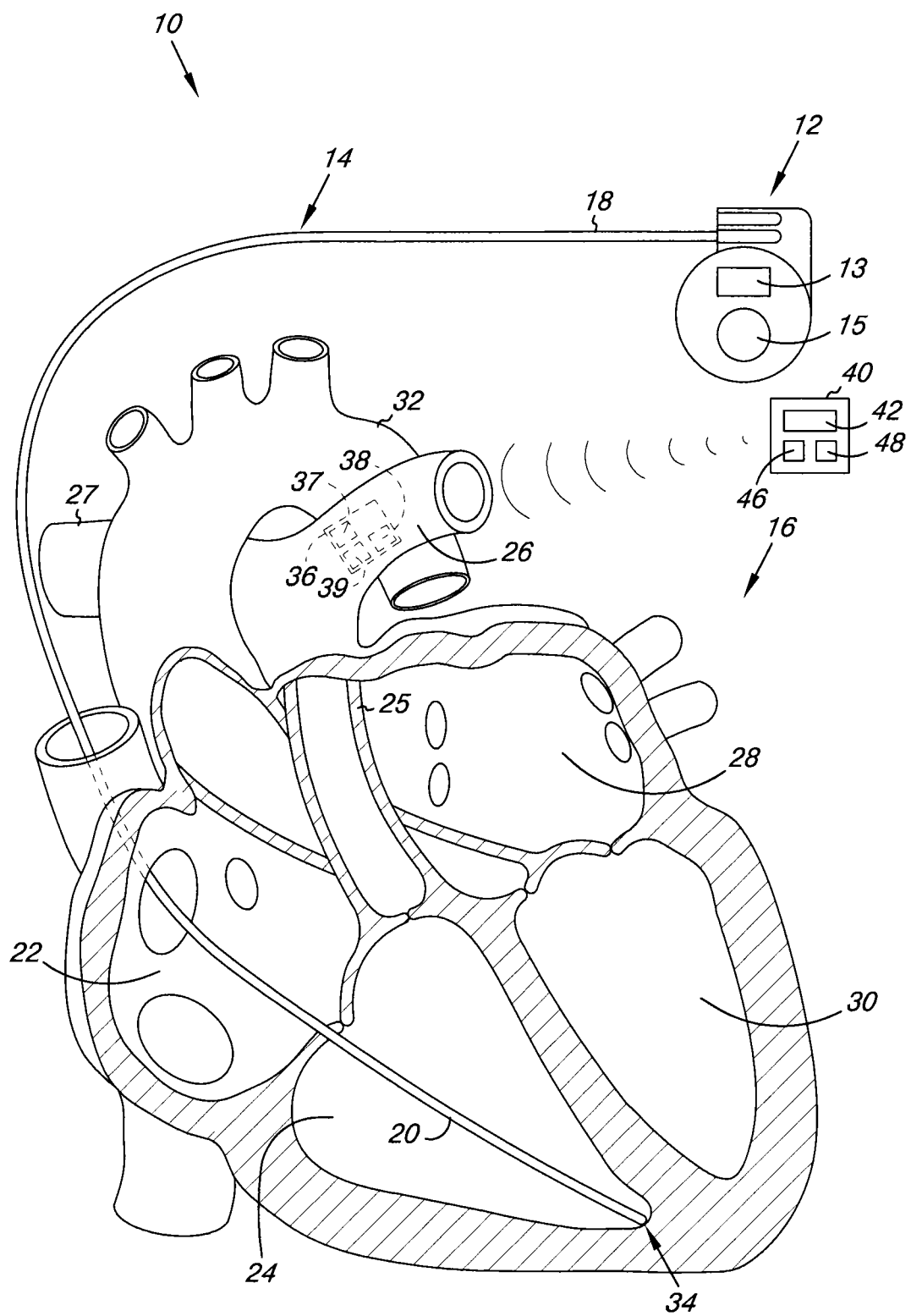
FIG. 1 is a combined cutaway and perspective view of a multi-element acoustic energy delivery system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a combined cutaway and perspective view of an acoustic energy delivery system 10 according to one embodiment of the present invention. In the embodiment shown in FIG. 1, the system 10 includes a pulse generator 12 having a power source 13, a cardiac lead 14, and an acoustic transducer 15. The lead 14 operates to convey electrical signals between the heart 16 and the pulse generator 12. A proximal end 18 of the lead 14 is coupled to the pulse generator 12 and a distal end 20 is coupled to the heart 16. The heart 16 includes a right atrium 22, a right ventricle 24, and a main pulmonary artery 25. The heart 16 also includes a left atrium 28, a left ventricle 30, and an aorta 32. In the embodiment shown, the system 10 includes one lead 14, but in other embodiments, the system 10 includes a plurality of leads 14. For example, the system 10 may include a first lead 14 adapted to convey electrical signals between the pulse generator 12 and the left ventricle 30 and a second lead 14 adapted to convey electrical signals between the pulse generator 12 and the right ventricle 24.

In the embodiment of FIG. 1, an electrode 34 is positioned in the right ventricle 24. When positioned as shown, the electrode 34 can be used to sense the electrical activity of the heart 16 and/or to apply a stimulating pulse to the right ventricle 24. In other embodiments, the cardiac lead 14 can also be implanted in other portions of the heart 16 as known in the art. For example, the lead 14 may be implanted in the right atrium 22, the left atrium 28, the left ventricle 30, or in the coronary veins (e.g., for bi-ventricular pacing and/or heart failure treatment). In one embodiment, the cardiac lead 14 includes multiple electrodes 34. In some embodiments, the lead 14 is an epicardial lead.

The system 10 includes a remote implantable medical device 36, which has a power source 37, an acoustic transducer 38, and circuitry 39 in addition to other components related to the IMD 36 function. In some embodiments, the system 10 also includes an energy delivery device 40, which has a multi-element transducer array 42, a power source 46, and a controller 48. In the embodiment shown in FIG. 1, the energy delivery device 40 is used to deliver acoustic energy to the IMD 36 (shown in FIG. 1 as waves emanating from the energy delivery device 40 toward the IMD 36). The transducer 38 in the IMD 36 converts acoustic energy to electrical energy, which can then be used immediately, in the short term, or stored for later use by the IMD 36 depending on the power source 37. The power source 37 in the IMD 36 can be a rechargeable battery, a capacitor, or any other energy source for providing electrical operating power to various components of the IMD 36. The energy delivery device 40 is electronically reconfigurable by utilizing the controller 48 to adjust excitation parameters such as timing, phase, amplitude, and/or frequency of the multi-element transducer 42, and is thus able to deliver a range of acoustic fields to the IMD 36 to increase efficiency in recharging. In other embodiments, the energy delivery device 40 can deliver acoustic energy to the acoustic transducer 15 of the pulse generator 12 or to any other implantable medical device in place of or in addition to the IMD 36.

The IMD 36 shown in FIG. 1 is a pressure sensor for measuring pulmonary arterial pressure. Although the IMD 36 is shown in the left pulmonary artery 26, in other embodiments, the IMD 36 may be implanted in the main pulmonary artery 25 or in the right pulmonary artery 27. In other embodiments, the IMD 36 can be configured to measure other physiological parameters such as, for example, temperature, blood or fluid flow, strain, and/or electrical, chemical or magnetic properties within the body.

In other embodiments, the IMD 36 may be implanted in other regions of the patient's vasculature, in other body lumens, or in other areas of the body, and may comprise any type of chronically implanted device or remote sensor adapted to deliver therapy or monitor biological and chemical parameters, properties, and functions. For example, the IMD 36 could comprise a glucose level monitor, a pulmonary sound sensor, a satellite pacing device, or any other remote sensing or therapy-delivering device. In other embodiments, the IMD 36 could sense, measure, calculate, or derive associated parameters such as, for example, the flow rate, the maximum and minimum pressure, and the time rate change (slope) of the pressure. In some embodiments, a plurality of remote implantable medical devices 36 are implanted throughout the body, and are configured to receive acoustic signals from the energy delivery device 40.

Figure 2:
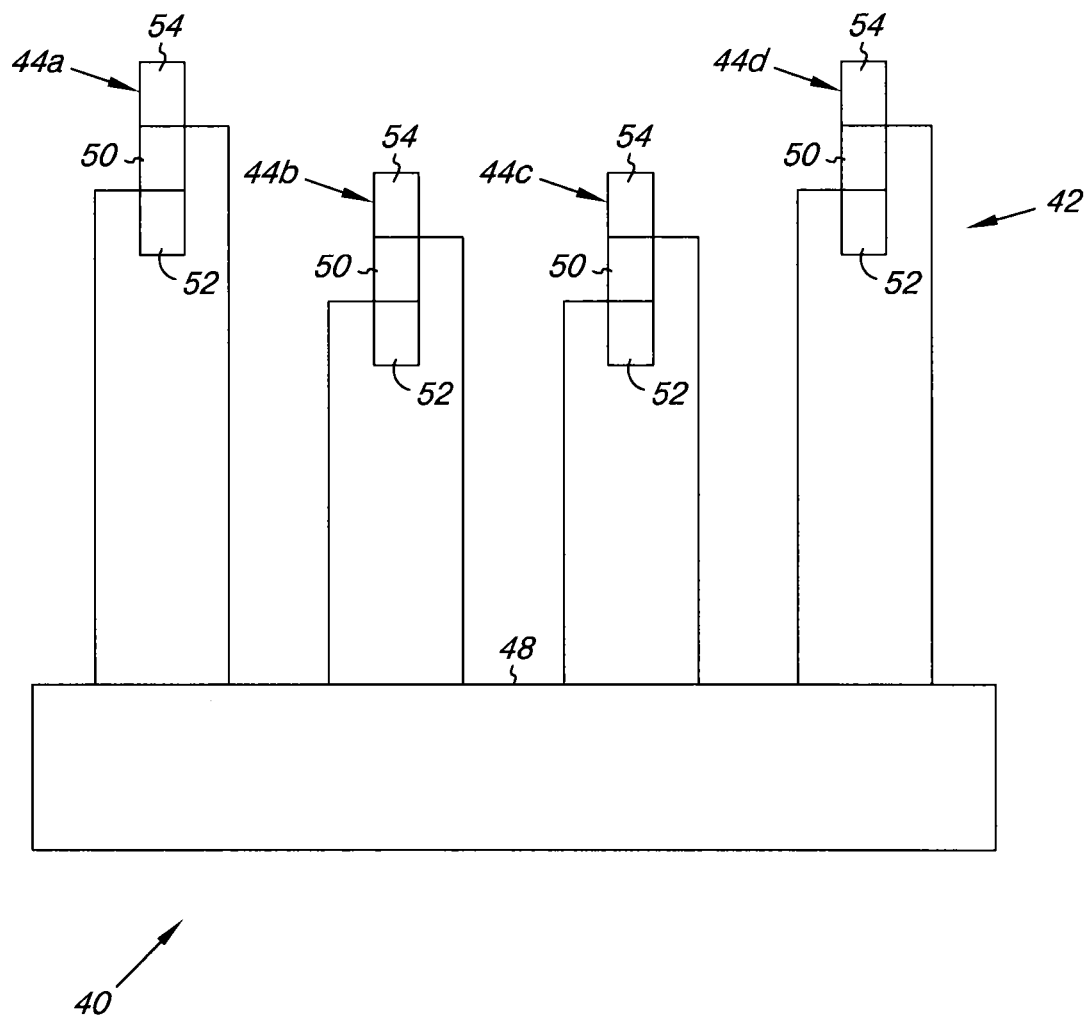
FIG. 2 is a schematic view of the multi-element energy delivery device of FIG. 1 according to one embodiment of the present invention.

FIG. 2 is a schematic view of one embodiment of the energy delivery device 40 of FIG. 1. In the illustrated embodiment, the energy delivery device 40 includes an array 42 of ultrasonic elements 44. The array 42 is used to transmit an acoustic energy signal to and efficiently recharge the power source 37 in the IMD 36. Use of the array 42 in some embodiments may enable an increase in energy transfer efficiency. The ultrasonic elements 44 are electrically coupled to the controller 48, which can be a microprocessor, an integrated circuit, or any other processor or circuitry that can be used for operating the array 42. In some embodiments, the controller 48 selectively controls each ultrasonic element 44 individually such that the multi-element array 42 functions as a combination of ultrasonic elements 44. In one embodiment, for example, the controller 48 operates all ultrasonic elements 44 simultaneously and in-phase as if the array 42 were a single ultrasonic element. In other embodiments, the controller 48 operates all or some of the ultrasonic elements 44 with phase delays and/or amplitude modulations, electronically changing the effective aperture of the array 42. In still other embodiments, the controller 48 operates a single ultrasonic element 44 or a subset of ultrasonic elements 44. The controller 48 determines the appropriate configuration for transmission of acoustic energy from the array 42 to the IMD 36 and controls the operation of the ultrasonic elements 44 accordingly, as discussed further herein, for example, with respect to FIGS. 3-4. In some embodiments, the controller 48 utilizes feedback to determine the appropriate transmission configuration. In other embodiments, the controller 48 operates the transducer elements 44 without feedback.

In the embodiment shown in FIG. 2, the array 42 includes four ultrasonic elements 44, but in other embodiments, the array 42 can include any number of ultrasonic elements 44. In one embodiment, the ultrasonic elements 44 operate at the same frequency. In other embodiments, the ultrasonic elements 44 do not all operate at the same frequency. In one embodiment, the ultrasonic elements 44 operate at a frequency of between about 20 kHz to about 200 kHz. In one embodiment, the ultrasonic elements 44 operate at a center frequency of about 40 kHz. In one embodiment, all of the ultrasonic elements 44 have the same resonant frequency, but in other embodiments, the ultrasonic elements 44 do not all have the same resonant frequency.

In the embodiment illustrated in FIG. 2, the ultrasonic elements 44 are piezoelectric elements including an active piezoelectric layer 50, a backing layer 52, and a front matching layer 54. The general principles of operation of piezoelectric elements are well known in the art. Briefly, the application of an AC voltage across electrodes coupled to the piezoelectric layer 50 causes the piezoelectric layer 50 to oscillate at the frequency of the applied voltage and produce an outward acoustic wave. In one embodiment, the piezoelectric layer 50 is made from a piezopolymer, piezoceramic, or piezocomposite material. In one embodiment, the piezoelectric layer 50 is a polyvinylidine difluoride ("PVDF") material. In another embodiment, the piezoelectric layer 50 is a lead zirconate titanate ("PZT") material. The ultrasonic elements 44 can have a variety of shapes and physical arrangements to maximize energy delivery to the IMD, as shown, for example, in FIGS. 5-9.

In the embodiment shown in FIG. 2, the backing layer 52 provides mechanical support and absorbs reflected acoustic energy. In one embodiment, the matching layer 54 provides an acoustic impedance match between the active layer 50 and the patient's skin, increasing energy transmission into the body. The matching layer 54 may be comprised of multiple layers to achieve the optimal acoustic impedance match. The piezoelectric layer 50, backing layer 52, and front matching layer 54 have a high coupling coefficient. The high coupling coefficient results in a high sensitivity of the ultrasonic element 44 and a high signal to noise ratio. The high coupling coefficient also allows for a larger bandwidth, thereby allowing for a high energy transfer level and a low reverberation level. The delivery of acoustic energy from an external energy delivery device 40 to an IMD 36 located within a patient often requires transmission through a complex, indirect, and lossy propagation path. Propagation is often indirect and multipath through attenuating body tissues and reflecting tissue interfaces resulting from different acoustic impedances in tissues such as skin, bones, lungs, muscles, and blood. Despite these complexities, the energy delivery device 40 can be used to reduce propagation losses and more efficiently deliver energy to the power source 38 within the implantable medical device 36.

Figure 3:
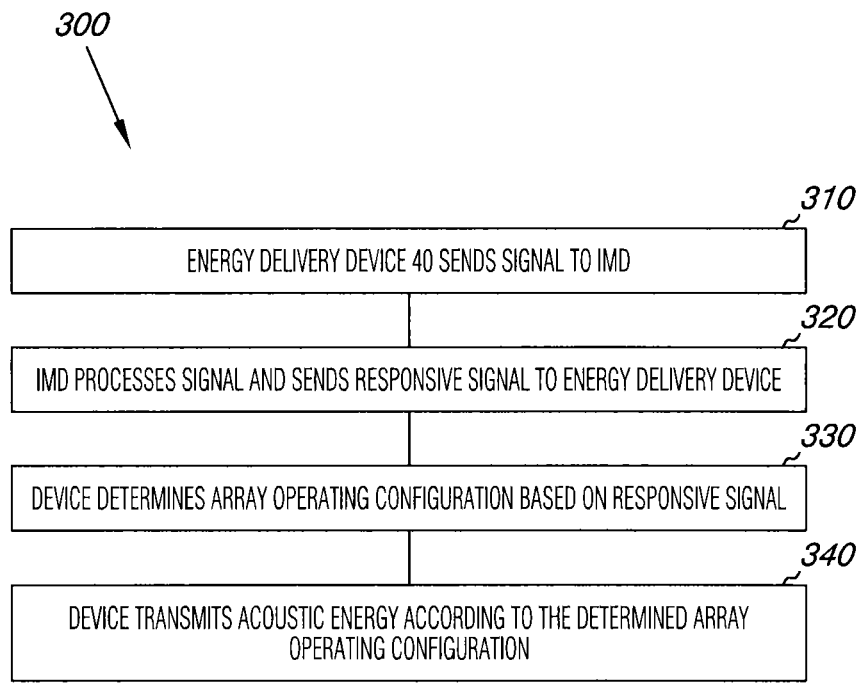
FIG. 3 is a flowchart illustrating a method of controlling the multi-element array of FIG. 2 according to one embodiment of the present invention.

FIG. 3 illustrates an illustrative method 300 of controlling the multi-element array 42 of FIG. 2 according to one embodiment of the present invention. As shown in FIG. 3, the energy delivery device 40 sends a signal to the implantable medical device 36 (block 310). The signal can be a ping, a series of pings, an instruction, or a command. The remote implantable medical device 36 receives and processes the signal and sends a responsive signal back to the device 40 (block 320). The responsive signal can be a generic transmission signal, an encoded measurement of the signal strength received from the energy delivery device 40, or some other signal. The energy delivery device 40 then determines the operating configuration of the array 42 producing the most efficient recharging based on the responsive signal (block 330) and configures the controller 48 to operate the ultrasonic elements 44 to transmit the acoustic energy according to that determined configuration (block 340).

In one implementation of method 300, for example, the controller 48 determines which ultrasonic elements 44 have a minimum attenuation in the acoustic path to the IMD 36 and operates only those ultrasonic elements 44 having the minimum attenuation in the acoustic path or those elements 44 having the least attenuating path. In one embodiment, the controller 48 determines which elements have minimum attenuation by first transmitting a signal from each element 44 individually to the IMD 36 and then receiving a response from the IMD 36. In one embodiment, the response from the IMD is a measurement of the acoustic signal amplitude of the IMD 36 received from the signal transmitted by each individual element 44 of the energy delivery device 40. In this embodiment, a response with a higher signal amplitude measurement may indicate less attenuation along the acoustic path than a response with a lower signal amplitude measurement. In another embodiment, the response from the IMD 36 is its standard response signal (e.g., an acknowledgement signal of known frequency and amplitude), and controller 48 determines the ultrasonic elements 44 having minimum attenuation by comparing the amplitude of the response signal received by the individual ultrasonic elements 44. The determination of whether the acoustic signal is sufficient can be determined, for example, by comparing the acoustic signal level received against a preset threshold programmed within the controller 48. In an alternative embodiment, the controller 48 operates a subset of the ultrasonic elements 44 that have a minimum attenuation in the acoustic path rather than a single ultrasonic element 44.

In another implementation of method 300, the controller 48 incorporates time reversal techniques to optimize the delivery of the acoustic energy to the IMD 36. Time reversal techniques enable phase alignment of acoustic fields at a desired target when the target's location is not precisely known or is changing. An illustrative technique for optimizing recharging efficiency using time reversal techniques is described, for example, in U.S. Provisional Patent Application Ser. No. 61/027,983, entitled, "Systems and Methods For Controlling Wireless Signal Transfers Between Ultrasound Enabled Medical Devices," which is incorporated herein by reference in its entirety. In some embodiments, the time reversal process is implemented according to method 300. The energy delivery device 40 transmits an acoustic signal towards the IMD 36. The IMD 36 receives the acoustic signal and, in response, transmits a series of signals back to the energy delivery device 40. The signals from the IMD 36 are received by the individual ultrasonic elements 44. The controller 48 may then analyze the received signals, determine the phase and amplitude differences between the received signals, and compute compensation factors. The controller 48 then applies these compensation factors to control the ultrasonic elements 44 in order to deliver the acoustic energy to the IMD 36.

Figure 4:
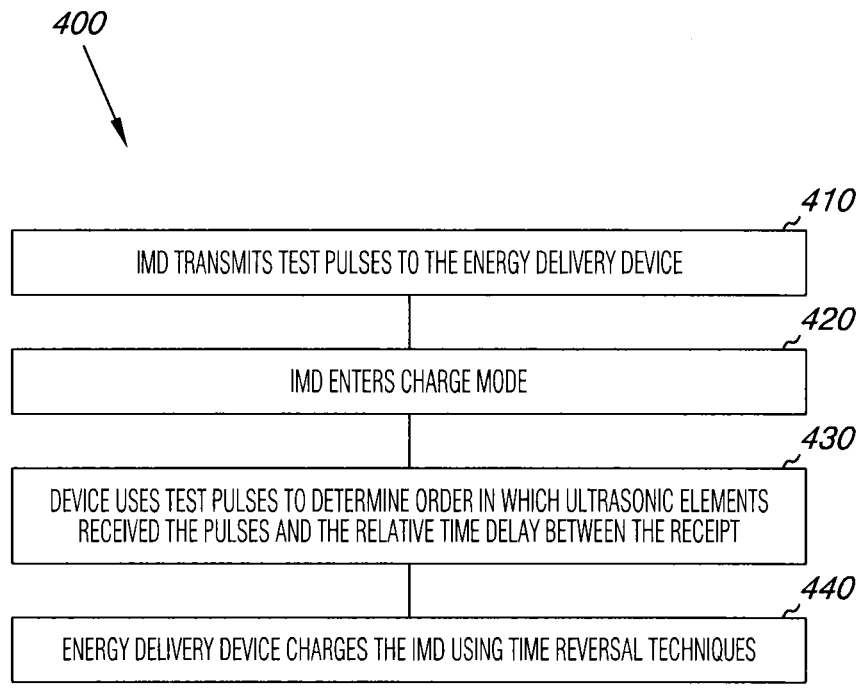
FIG. 4 is a flowchart illustrating a method of using a multi-element energy delivery device to send a test pulse to an implantable medical device according to one embodiment of the present invention.

FIG. 4 is a flowchart showing an exemplary method 400 of processing a test pulse sent from the IMD 36 to the energy delivery device 40 using time reversal techniques according to one embodiment of the present invention. As shown in FIG. 4, the IMD 36 transmits test pulses to the energy delivery device 40 (block 410). The test pulses can be any type of pulse. In one embodiment, for example, the test pulses are eight "1" bit pulses. The IMD 36 then enters into a charging mode (block 420). The energy delivery device 40 receives the test pulses on each ultrasonic element 44 of the device 40 and uses these pulses to determine the relative time delays between the signals received at each element 44 (block 430). The energy delivery device 40 transmits acoustic energy from the ultrasonic elements 44 using time reversal techniques. In one embodiment, for example, the energy delivery device 40 transmits acoustic energy in the opposite order from the order in which the device 40 received the test pulses and incorporating the relative time delays (block 440). Using the energy delivery device 40 shown in FIG. 2 as an example, if the charges received on elements 44a, 44b, 44c, and 44d are received in the order 44a, 44c, 44d, and 44b having a relative delay between 44a and 44c of one second, the charging would occur in the order 44b, 44d, 44c, 44a with a one second transmit delay between 44c and 44a.

The methods described herein can be used at any time during the charging cycle. In one embodiment, the controller 48 electronically reconfigures the control of the array 42 to compensate for changes in location of the IMD 36 from a previous position due to a change in body position, organ movement, respiration, and/or for other reasons. In some embodiments, the controller 48 incorporates information regarding physiological patterns (e.g., respiratory rate, cardiac cycle, etc.) and controls the array 42 based upon the pattern information. In one embodiment, the method is used at the beginning of the charging cycle. In another embodiment, the method is used during the charging cycle. In one embodiment, the method is used during the charging cycle and is initiated when a charge pause occurs in the charging cycle. In some embodiments, the charge pause is a programmable event in the controller 48 and is used to re-evaluate the efficiency of charging. In some embodiments, the method is used if there is a loss of transmission during the charging cycle.

In various other embodiments, the controller 48 can operate the array 42 without feedback from the IMD 36 to achieve the desired charging efficiency. In one embodiment, for example, the controller 48 operates the array 42 by cycling through all or some of the ultrasonic elements 44, individually or as subsets, to avoid overheating at any one location on the patient's body. In another embodiment, the controller 48 can implement known beamsteering, beamshaping, and/or beamforming techniques to adjust the acoustic energy signal from the array 42. Generally, these processes involve using the controller 48 to apply time delays on the individual elements 44 to shape and/or steer the acoustic field produced by the array 42.

In one embodiment, the beamsteering is the sweeping of the acoustic field through a series of spatial locations, thus defining the range of interrogation. In one embodiment, beamforming is the definition of the acoustic field width to match a desired region of interrogation. In one embodiment, the beam width and steering range are varied. The energy delivery device 40 can be designed with a range of beamforming and beamsteering capabilities based on its intended use. In one embodiment, variable shape ultrasonic elements 44 and/or ultrasonic elements 44 having acoustic lens/mirrors are used in conjunction with the controller 48 and methods described herein to alter the acoustic field.

Figure 5:
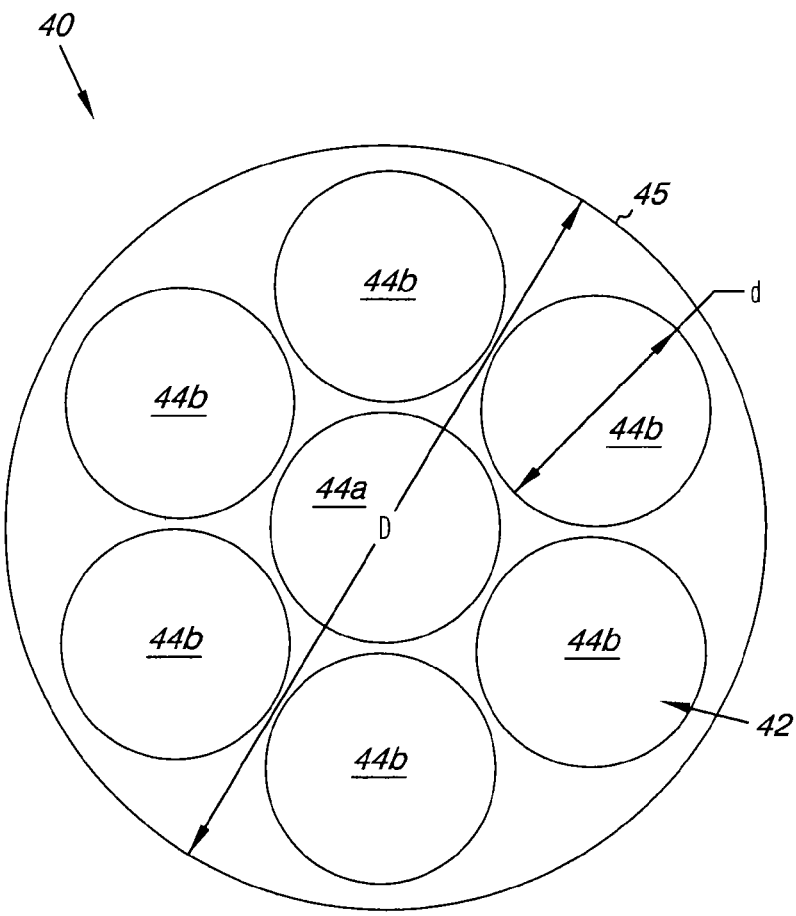
FIG. 5 is a top view of a multi-element energy delivery device according to one embodiment of the present invention.
Figure 6:
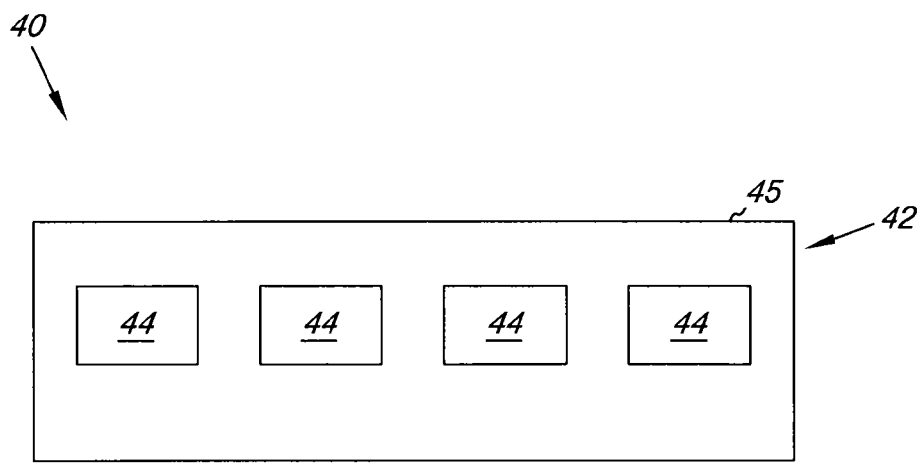
FIG. 6 is a top view of a multi-element energy delivery device according to another embodiment of the present invention.
Figure 7:
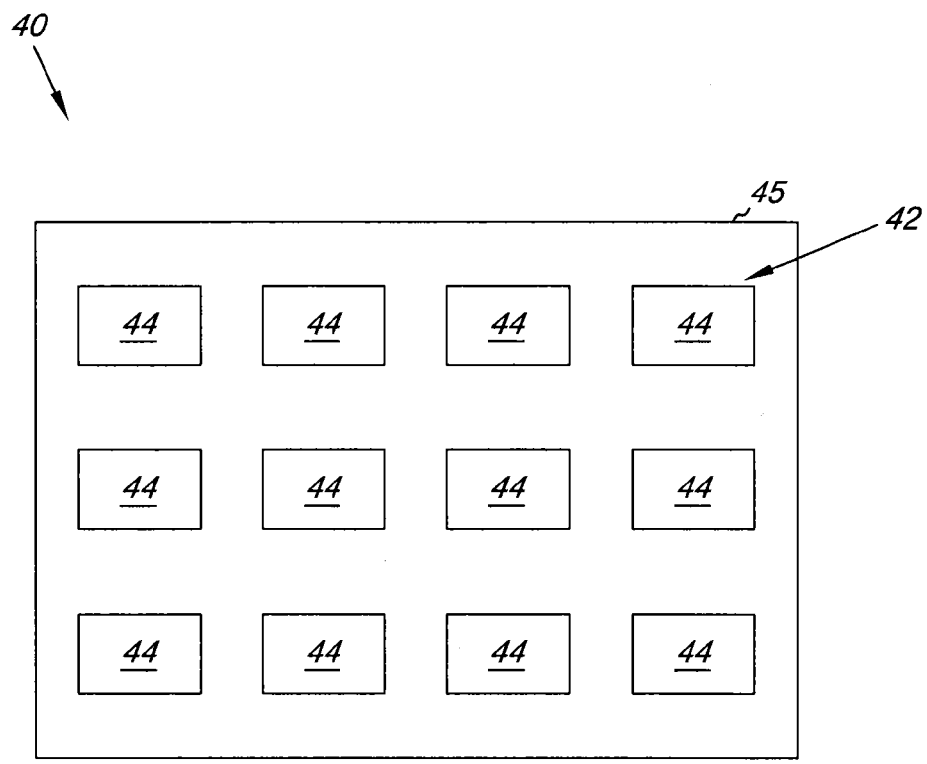
FIG. 7 is a top view of a multi-element energy delivery device according to another embodiment of the present invention.
Figure 8:
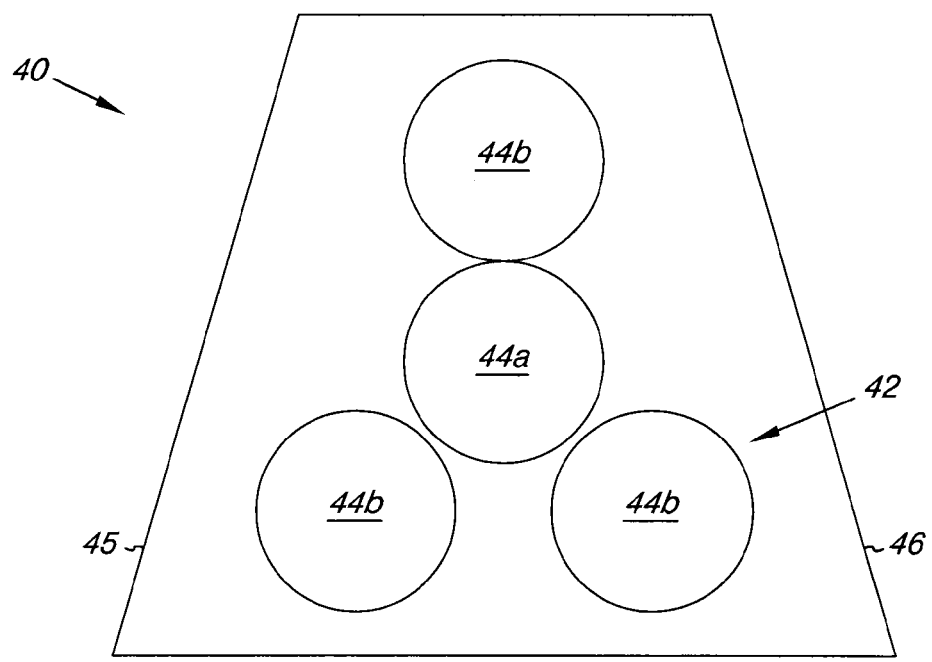
FIG. 8 is a top view of a multi-element energy delivery device according to another embodiment of the present invention.

FIG. 5 is a top view of an energy delivery device 40 according to one embodiment of the present invention. In the embodiment illustrated in FIG. 5, the energy delivery device 40 includes an array 42 of ultrasonic elements 44 located on a support structure 45. A central ultrasonic element 44a is located at the center of the support structure 45 and six additional ultrasonic elements 44b are circumferentially spaced around the central ultrasonic element 44a. In one embodiment, the energy delivery device 40 has a diameter D between about 6 and about 7.5 centimeters and a height of less than about 5 centimeters. In one embodiment, the ultrasonic elements 44 have a generally circular shape and a diameter d between about 1.8 and about 2.5 centimeters. In one embodiment, the energy delivery device 40 weighs less than about 400 grams and can be readily incorporated into a wearable garment or handheld device. In one embodiment, the energy delivery device 40 is capable of producing 40 kHz ultrasonic waves of 50 kPa at 20 centimeters of water along the maximum response axis when all of the ultrasonic elements 44 are driven in phase.

The ultrasonic elements 44 can have a variety of shapes and configurations. FIGS. 6-9 illustrate alternative embodiments of the array 42. In the embodiment shown in FIG. 6, the energy delivery device 40 has an array 42 of four rectangular ultrasonic elements 44 arranged in a linear manner. In the embodiment shown in FIG. 7, the energy delivery device 40 has an array 42 of three linearly arranged rows of rectangular ultrasonic elements 44 arranged in a three by four matrix. In the asymmetric embodiment illustrated in FIG. 8, the energy delivery device 40 has an array 42 of one central ultrasonic element 44a and a plurality of additional ultrasonic elements 44b positioned around the central ultrasonic element 44 at unequal distances from the central ultrasonic element 44a.

In the embodiments shown in FIGS. 5-8, the elements 44 are located in the same plane. In other embodiments, the acoustic beam is mechanically focused to a desired depth by configuring the ultrasonic elements 44 towards the center of an imaginary sphere such that a focus is created at the center of the sphere. For example, the ultrasonic elements 44 can be attached on a focusing structure such as a spherical shell. In another embodiment, the ultrasonic elements 44 can include an acoustic lens/mirror to mechanically focus the acoustic beam to a desired depth within the patient.

Figure 9:
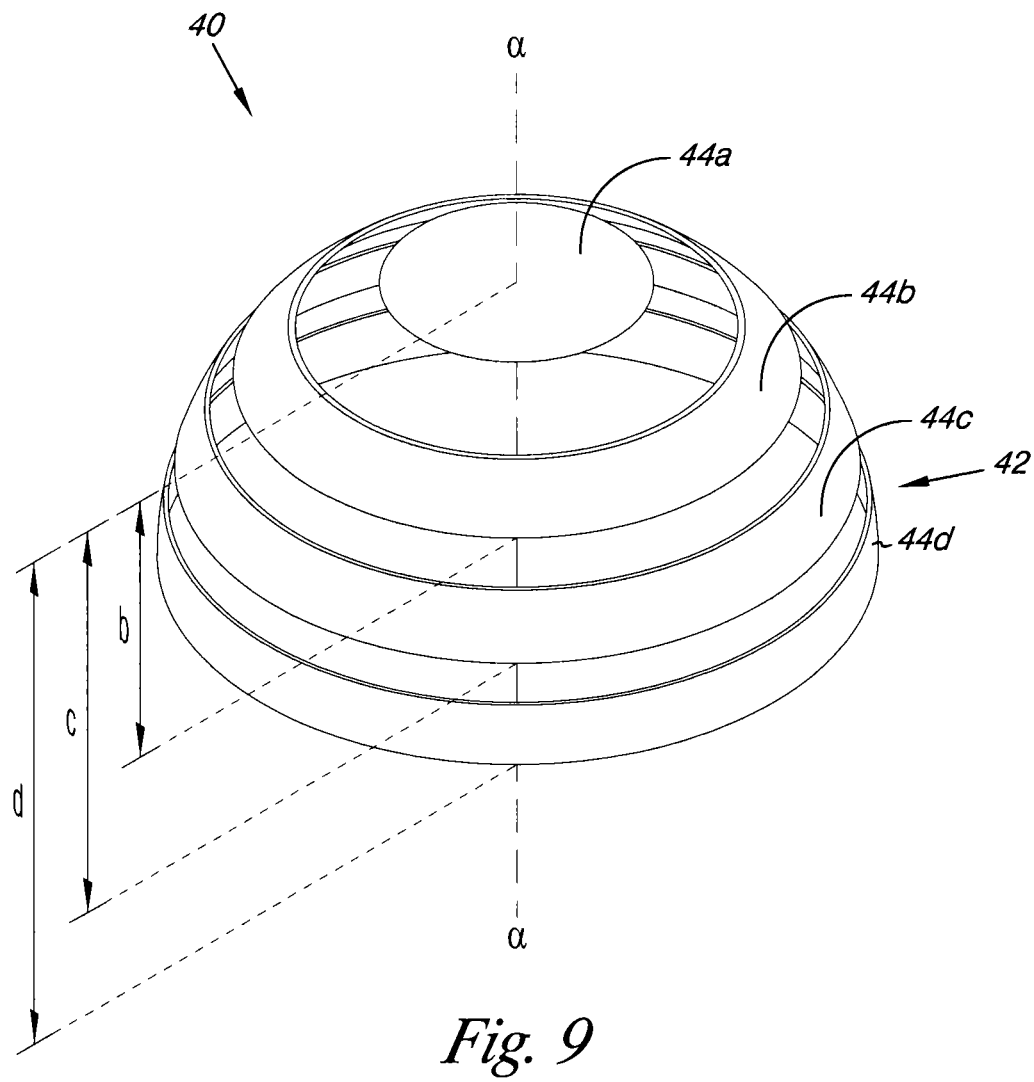
FIG. 9 is a perspective view of a multi-element energy delivery device according to another embodiment of the present invention.

FIG. 9 illustrates a dome or beehive-shaped array 42. As shown in FIG. 9, the array 42 includes a circular ultrasonic element 44a. An axis $\alpha$-$\alpha$ that is perpendicular to the circular ultrasonic element 44a extends through the center of the circular ultrasonic element 44a. An annular ultrasonic element 44b is centered on the axis $\alpha$-$\alpha$ and positioned along the axis $\alpha$-$\alpha$ at a distance b from the circular ultrasonic element 44a. Similarly, an annular ultrasonic element 44c has a greater diameter than ultrasonic element 44b, is centered on the axis $\alpha$-$\alpha$, and is positioned along the axis $\alpha$-$\alpha$ at a distance c from the circular ultrasonic element 44a. An annular ultrasonic element 44d has a greater diameter than ultrasonic element 44c, is centered on the axis $\alpha$-$\alpha$, and is positioned along the axis $\alpha$-$\alpha$ at a distance d from the circular ultrasonic element 44a. As shown in FIG. 9, the ultrasonic elements 44b, 44c, and 44d are non-planar. In another embodiment, the ultrasonic elements 44b, 44c, 44d are planar. In yet another embodiment, the ultrasonic element 44a is non-planar.

Although FIGS. 5-9 illustrate specific numbers and configurations of ultrasonic elements 44, any number and configuration of ultrasonic elements 44 can be incorporated into the energy delivery device 40 for use in delivering acoustic energy to an implantable medical device. The array 42 can have a polygonal, a circular, or an annular configuration. The configuration can be symmetric or asymmetric about one or more axes. The ultrasonic elements 44 can have a polygonal, circular, or annular cross-sectional shape. In other embodiments, the ultrasonic elements 44 can be cylindrical, flat, or curved. In one embodiment, all of the ultrasonic elements 44 have the same shape. In other embodiments, the ultrasonic elements 44 have different shapes. For example, a central ultrasonic element 44a could have a generally circular shape and additional ultrasonic elements 44b could have a rectangular shape.

In one embodiment, the energy delivery device 40 is located on a handheld device (not shown). In another embodiment, the energy delivery device 40 is located on a wearable garment (not shown) such as a vest, shirt or belt, which can be tightly coupled to the patient's skin. The array 42 may be located directly on the handheld device or garment. Alternatively, the array 42 may be located on a support structure such as a flat plate or bed, which may or may not be coupled to a handheld device or garment.

Although the energy delivery device 40 has been described as delivering acoustic energy to a remote IMD 36, in other embodiments the energy delivery device 40 is used to deliver energy to other implantable medical devices capable of receiving acoustic energy and converting the acoustic energy to operating power. For example, the energy delivery device 40 can be used to deliver acoustic energy to a power source within a drug delivery device, a neurostimulator, a pacemaker, or a defibrillator.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An energy delivery device configured to provide an acoustic energy to an implantable medical device IMD, the IMD configured to convert the acoustic energy into electrical energy for powering one or more components of the IMD, the energy delivery device comprising:
   an array of acoustic transducer elements, each of the acoustic transducer elements configured to receive a signal from the IMD; and
   a controller coupled to the array of acoustic transducer elements, wherein the controller is configured to control one or more of the acoustic transducer elements of the array to transmit the acoustic energy to the IMD based at least in part on the signal received from the IMD.

2. The device of claim 1, wherein the controller is further configured to control the array of acoustic transducer elements to compensate for a change in a location of the IMD.

3. The device of claim 1, wherein the controller is configured to implement one or more beamsteering techniques to cause the one or more acoustic transducer elements of the array to focus the acoustic energy.

4. The device of claim 1, wherein the controller is configured to implement one or more beamshaping techniques to cause the one or more acoustic transducer elements of the array to focus the acoustic energy.

5. The device of claim 1, wherein the controller is configured to implement one or more beamforming techniques to cause the one or more acoustic transducer elements of the array to focus the acoustic energy.

* * * * *